United States Patent
Melkent et al.

(10) Patent No.: US 6,348,058 B1
(45) Date of Patent: Feb. 19, 2002

(54) IMAGE GUIDED SPINAL SURGERY GUIDE, SYSTEM, AND METHOD FOR USE THEREOF

(75) Inventors: Tony Melkent, Lafayette, CO (US); Kevin T. Foley, Germantown, TN (US); Bradley T. Estes, Memphis, TN (US); Joseph Chaudoin, Germantown, TN (US)

(73) Assignee: Surgical Navigation Technologies, Inc., Broomfield, CO (US)

( * ) Notice: Subject to any disclaimer, the term of this patent is extended or adjusted under 35 U.S.C. 154(b) by 0 days.

(21) Appl. No.: 09/209,248

(22) Filed: Dec. 10, 1998

Related U.S. Application Data

(60) Provisional application No. 60/069,595, filed on Dec. 12, 1997.

(51) Int. Cl.[7] .................................................. A61B 5/05
(52) U.S. Cl. ......................... 606/130; 606/97; 606/99; 600/429
(58) Field of Search ........................ 606/61, 60–66, 606/96–102, 129, 130, 11, 80–85; 600/426, 427, 429

(56) References Cited

U.S. PATENT DOCUMENTS

| | | | |
|---|---|---|---|
| 4,368,556 A | 1/1983 | Wanner et al. ............ 16/111 R |
| 5,198,877 A | 3/1993 | Schulz ....................... 356/375 |
| 5,249,581 A | 10/1993 | Horbal et al. | |
| 5,299,288 A | * 3/1994 | Glassman et al. ........... 395/80 |
| 5,305,203 A | 4/1994 | Raab ..................... 364/413.13 |
| 5,309,913 A | 5/1994 | Kormos et al. | |
| 5,383,454 A | 1/1995 | Bucholz | |
| 5,389,101 A | 2/1995 | Heilbrun et al. ............ 606/130 |
| 5,399,146 A | 3/1995 | Nowacki et al. ............... 601/4 |
| 5,402,801 A | 4/1995 | Taylor ........................ 128/898 |
| 5,447,154 A | 9/1995 | Cinquin et al. | |

(List continued on next page.)

FOREIGN PATENT DOCUMENTS

| | | |
|---|---|---|
| EP | 0 676 178 A1 | 10/1995 |
| WO | WO 88/09151 | 12/1988 |
| WO | WO 91/04711 | 4/1991 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO96/11624 | * 4/1996 |
| WO | WO 97/40764 | 11/1997 |
| WO | WO 99/15097 | 4/1999 |

OTHER PUBLICATIONS

3–D Digitizing Accessories, Pixsys.

*Primary Examiner*—David O. Reip
(74) *Attorney, Agent, or Firm*—Harness, Dickey & Pierce, P.L.C.

(57) ABSTRACT

A guide is disclosed for use in performing spinal surgery to prepare across a spinal disc and adjacent vertebrae an implantation space. The guide is associated with a computer controlled surgical navigation system employing an energy-detecting array to track positions of the guide in three dimensional space relative to a known reference point. The guide comprises a body for providing protected access to prepare across the spinal disc and into the adjacent vertebrae the implantation space. The body has a passage adapted to receive a bone removal device for forming the implantation space through the body. At least one electrically energizable energy emitter array is attached to the body for use in identifying the location of the guide relative to the adjacent vertebrae. A system and method for using the guide in spinal surgery are also disclosed.

22 Claims, 10 Drawing Sheets

U.S. PATENT DOCUMENTS

| | | | |
|---|---|---|---|
| 5,483,961 A | 1/1996 | Kelly et al. | |
| 5,484,437 A | 1/1996 | Michelson | |
| 5,494,034 A | 2/1996 | Schlöndorff et al. | |
| 5,515,160 A | 5/1996 | Schulz et al. | 356/241 |
| 5,517,990 A | 5/1996 | Kalfas et al. | |
| 5,531,227 A | 7/1996 | Schneider | |
| 5,531,520 A | 7/1996 | Grimson et al. | 382/131 |
| 5,568,809 A | 10/1996 | Ben-haim | |
| 5,571,109 A | 11/1996 | Bertagnoli | |
| 5,572,999 A | 11/1996 | Funda et al. | |
| 5,588,430 A | 12/1996 | Bova et al. | |
| 5,603,318 A | 2/1997 | Heilbrun et al. | |
| 5,617,857 A | 4/1997 | Chader et al. | |
| 5,622,170 A | 4/1997 | Schulz | |
| 5,630,431 A | 5/1997 | Taylor | 128/897 |
| 5,638,819 A | 6/1997 | Manwaring et al. | |
| 5,647,361 A | 7/1997 | Damadian | |
| 5,662,111 A | 9/1997 | Cosman | |
| 5,676,673 A | 10/1997 | Ferre et al. | 606/130 |
| 5,682,886 A | 11/1997 | Delp et al. | |
| 5,695,500 A | 12/1997 | Taylor et al. | 606/130 |
| 5,695,501 A | 12/1997 | Carol et al. | 606/130 |
| 5,711,299 A | 1/1998 | Manwaring et al. | |
| 5,732,703 A | 3/1998 | Kalfas et al. | |
| 5,748,767 A | 5/1998 | Raab | 382/128 |
| 5,749,362 A | 5/1998 | Funda et al. | |
| 5,755,725 A | 5/1998 | Druais | 606/130 |
| 5,772,594 A | 6/1998 | Barrick | 600/407 |
| 5,772,661 A * | 6/1998 | Michelson | 606/61 |
| 5,776,064 A | 7/1998 | Kalfas et al. | |
| 5,795,294 A | 8/1998 | Luber et al. | 600/407 |
| 5,799,055 A | 8/1998 | Peshkin et al. | 378/42 |
| 5,800,535 A | 9/1998 | Howard, III | 623/10 |
| 5,823,958 A | 10/1998 | Truppe | 600/426 |
| 5,833,608 A | 11/1998 | Acker | 600/409 |
| 5,834,759 A | 11/1998 | Glossop | 250/203.1 |
| 5,836,954 A | 11/1998 | Heilbrun et al. | 606/130 |
| 5,848,967 A | 12/1998 | Cosman | 600/426 |
| 5,851,183 A | 12/1998 | Bucholz | 600/425 |
| 5,868,675 A | 2/1999 | Henrion et al. | 600/424 |
| 5,871,445 A | 2/1999 | Bucholz | 600/407 |
| 5,871,487 A | 2/1999 | Warner et al. | 606/130 |
| 5,891,157 A | 4/1999 | Day et al. | 606/130 |
| 5,904,691 A | 5/1999 | Barnett et al. | 606/130 |
| 5,920,395 A | 7/1999 | Schulz | 356/375 |
| 5,921,992 A | 7/1999 | Costales et al. | 606/130 |

* cited by examiner

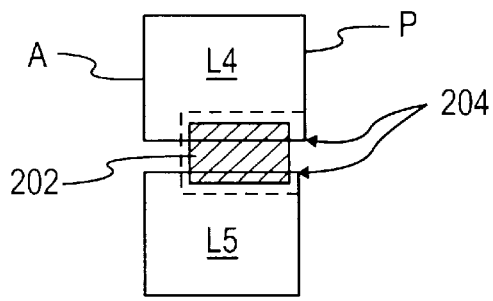
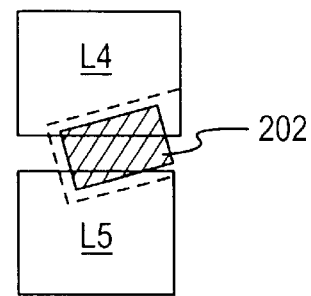
FIG. 4A  FIG. 4B
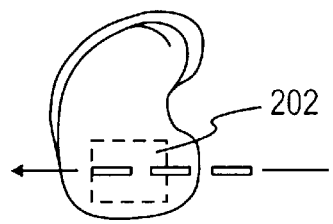
FIG. 5A
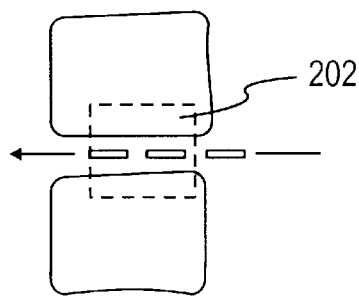
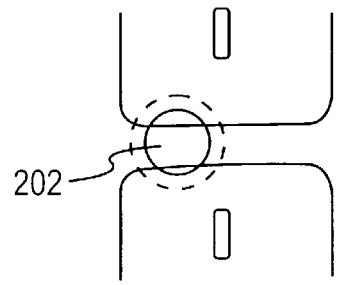
FIG. 5B  FIG. 5C

IMAGE GUIDED SPINAL SURGERY GUIDE, SYSTEM, AND METHOD FOR USE THEREOF

RELATED APPLICATIONS

This application relies on the benefit of priority of U.S. provisional patent application Ser. No. 60/069,595, filed on Dec. 12, 1997.

FIELD OF THE INVENTION

The present invention relates generally to providing a guide for use in performing spinal surgery, in conjunction with systems that use and generate images during medical and surgical procedures, which images assist in executing the procedures and indicate the relative position of various body parts and surgical instruments. In particular the invention relates to a guide, and system and method utilizing the guide, for performing spinal surgery to provide protected access across a spinal disc and into adjacent vertebrae to prepare an implantation space so as to ensure predetermined trajectory and placement of an artificial implant/bone dowel into the implantation space.

BACKGROUND OF THE INVENTION

Various instruments and methods have been used to prepare adjacent vertebrae of the spine for insertion of a bone dowel or artificial implant. These instruments and methods allow for the removal of disc material from between adjacent vertebrae as well as a portion of each vertebra to form an implantation space or opening. Drill sleeve, tubular member, sheath, working channel, and guard are a few of the names for the protective guide used to guide drills and other disc and bone removal devices into the spine to form the implantation space for receipt of the bone dowel or artificial implant. Certain of the guides have a sharpened end or include teeth for engaging the vertebrae upon application of an impaction force. The guide can be positioned so as to span the disc space and be seated into the adjacent vertebrae to provide protected access to the spine during the process of forming the implantation space. The implantation space spans the disc space and protrudes into each of the adjacent vertebrae along two opposed resected arcs. An example of the procedure for drilling holes across a disc space and instrumentation pertaining thereto are described in U.S. Pat. No. 5,484,437 to Michelson and is incorporated herein by reference.

The use of cylindrical implants is desirable because the surgeon can prepare the recipient site by drilling a cylindrical hole across the disc space and into the adjacent vertebrae. The curved surface of the cylindrical holes drilled into the vertebrae provide for the possibility of tight congruency when the cylindrical hole is fitted with an implant having corresponding cylindrical portions of matched diameter.

Typically, threaded artificial implants, such as the implant disclosed in U.S. Pat. No. 5,015,247 to Michelson, the entire disclosure of which is incorporated herein by reference, are placed into the implantation space between the adjacent vertebrae to directly participate and be incorporated in the ensuing fusion. Threaded bone dowels, such as those taught by Viche may also be placed into the implantation space for the purpose of bridging the opening and to be incorporated into the fusion between the vertebrae. Moreover, artificial implants of the push-in type, such as those disclosed in U.S. Pat. No. 5,593,409 to Michelson and assigned to the assignee of the present application and incorporated herein by reference, may also be inserted into the implantation space formed by the above described instruments and methods.

Whether pushing or threading an implant or dowel into the implantation space, the surgeon attempts to orient the sheath for guiding the formation of the implantation space to remove approximately the same amount of material from each of the vertebra. Once the implant or dowel is implanted, a fluoroscope may be used to assist in determining if proper placement has occurred.

A number of different types of surgical navigation systems have been described that include indications of the relative positions of medical instruments and body parts used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking means such as for example an LED array on the body part, emitters on the medical instruments, a digitizer to track the positions of the body part and the instruments, and a display for the position of an instrument used in a medical procedure relative to a body part.

Procedures for preparing an implantation space in the spine present certain particular challenges to be addressed at specific levels within the spinal column. For example, preforming such a procedure at L4-5 of the spine can raise the following issues: 1) During a posterior approach, significant muscle stripping and tearing is required to reach the L4-5 disc space. Significant post-operative trauma to the patient may result. 2) During an anterior approach, with either a transperitoneal or retroperitoneal, open or laparoscopic approach to the L4-5 disc space, the great vessels lie almost directly on the front of the spinal column at that level. Dissection and manipulation of these vessels may be time-consuming and difficult.

The applicant determined that a retroperitoneal "oblique approach" to the L-5 disc space can present a preferred surgical solution. The muscle splitting and tearing of the posterior approach is therefore not inevitable, since the oblique approach takes place just anterior to the psoas muscle located laterally along the vertebral column. The oblique approach also allows for an approach slightly posterior of the great vessels lying anterior on the spinal column, thus reducing any risk of injury to the great vessels.

In viewing the spine solely from a lateral fluoro image, the spine surgeon, via this oblique approach, would have a limited ability to see an indication of the depth and direction of their instrumentation as it moves in a posterior lateral fashion across the disc space towards the exiting nerve root.

In light of the foregoing, it would be beneficial in the art for a system and method for the placement of a guide in the spine that provides directional assistance to the surgeon to improve the placement of the guide used in forming the implantation space as well as for use in determining the depth of insertion of instruments passing through the guide, thereby improving the placement of implants and dowels into the implantation space.

SUMMARY OF THE INVENTION

Accordingly, the present invention is directed to a guide, system, and method for using the guide in performing spinal surgery to prepare an implantation space across a spinal disc and adjacent vertebrae. More specifically, one object of the present invention is directed to apparatus and procedures for the placement of a guide into the spine using image guided surgery to improve proper placement of the guide through which the implantation space is to be formed and thus proper placement of the implant or dowel.

To achieve this object and other advantages and in accordance with the purpose of the invention, as embodied and broadly described herein, the invention includes a guide for use in performing spinal surgery to prepare an implantation space across a spinal disc and adjacent vertebrae. The guide is used in conjunction with a computer controlled surgical navigation system employing an energy-detecting array to track positions of the guide in three dimensional space relative to a known reference point. The guide comprises a body for providing protected access to prepare the implantation space across the spinal disc and into the adjacent vertebrae. The body has a passage adapted to receive a bone removal device for forming the implantation space through the body. At least one emitter array is attached to the body for use in identifying the location of the guide relative to the adjacent vertebrae.

The guide may additionally include a disc penetrating extension extending from the body for insertion into the disc space between the adjacent vertebrae and for bearing against endplates of the adjacent vertebrae. A preferred body includes a hollow tube having an end including extensions for penetrating the spine. An emitter array is preferably on each extension of the guide and more preferably includes at least one LED. Preferred arrays include an electrically energizable energy emitter array, known as an active emitter, as well as a reflective surface that reflects signals, known as a passive emitter.

Additionally, the invention includes a system for use in performing spinal surgery to prepare across a spinal disc and adjacent vertebrae an implantation space. The system comprises the above described guide and a computer controlled surgical navigation system employing an energy detecting array to track positions of the guide in three dimensional space relative to a known reference point.

In addition, the invention further comprises a method for performing spinal surgery with a guide used to provide protected access across a spinal disc and into adjacent vertebrae to prepare an implantation space. The method comprises the steps of: attaching a reference array to the vertebrae of interest; registering the location of that vertebrae with a computer controlled surgical navigation system; contacting one end of the guide having at least one emitter array attached thereto to the adjacent vertebrae; employing the surgical navigation system with a computer controller and a digitizer array for communicating with the energy emitter of the guide; positioning the guide in three dimensional space relative to a known reference point system; and forming the implantation space through the guide across the disc space and into a portion of each of the adjacent vertebrae.

In another aspect, the method includes the step of generating a display of the position of the guide. The generating step preferably displays the location of the guide relative to the adjacent vertebrae to provide a view of the axial orientation of the guide relative to each vertebra and/or relative to the adjacent vertebrae. The orientation of the disc penetrating extensions can also be displayed. The location of the tip of an instrument which is placed through the guide can be displayed as well. Identifying the location of the instrument tip passing through the guide permits tracking of tool depth insertion. The generating step may also display the location of the guide relative to the adjacent vertebrae to provide a cross-sectional view of the guide relative to one of an anterior or posterior view of the adjacent vertebrae.

The method may also include the step of emitting a signal from an emitter attached to the guide which is received by an apparatus representatively indicating that signal on a visual display. A preferred method of the present invention also includes the step of implanting an artificial implant, a bone dowel, or other type of bone into the implantation space. The method also may include the step of tracking an artificial implant or bone dowel inserter via an emitter array attached to the inserter. The inserter preferably is configured to pass through the guide. The computer controlled surgical navigation system may be configured to display the inserter as it passes through the guide and more preferably may display both the inserter and the attached artificial implant or bone dowel based on the geometrical configuration of the inserter and of an implant or bone dowel attached thereto.

The objects of the invention are to provide a surgeon with the guide, system, and method to track the guide used in conjunction with a surgical navigation system in such a manner to operate on a patient on the spine to ensure proper orientation of the guide to the spine when forming an implantation space.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

FIG. 4A is a cross-sectional view of a spinal segment having an implant or dowel in a desirable position within the disc space and vertebral endplates;

FIG. 4B is a cross-sectional view of a spinal segment having an implant or dowel in a generally less desirable position within the disc space and vertebral endplates;

FIG. 5A is a cross-sectional view of an implant or dowel projected over an axial top view of a vertebra and showing a predetermined axial alignment of the implant or dowel to the vertebra;

FIG. 5B is a cross-sectional view of an implant or dowel positioned between adjacent vertebrae and showing a predetermined sagittal alignment of the implant or dowel to the vertebrae;

FIG. 5C is a cross-sectional view of an implant or dowel positioned between adjacent vertebrae and showing a predetermined coronal alignment of the implant or dowel to the vertebrae;

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
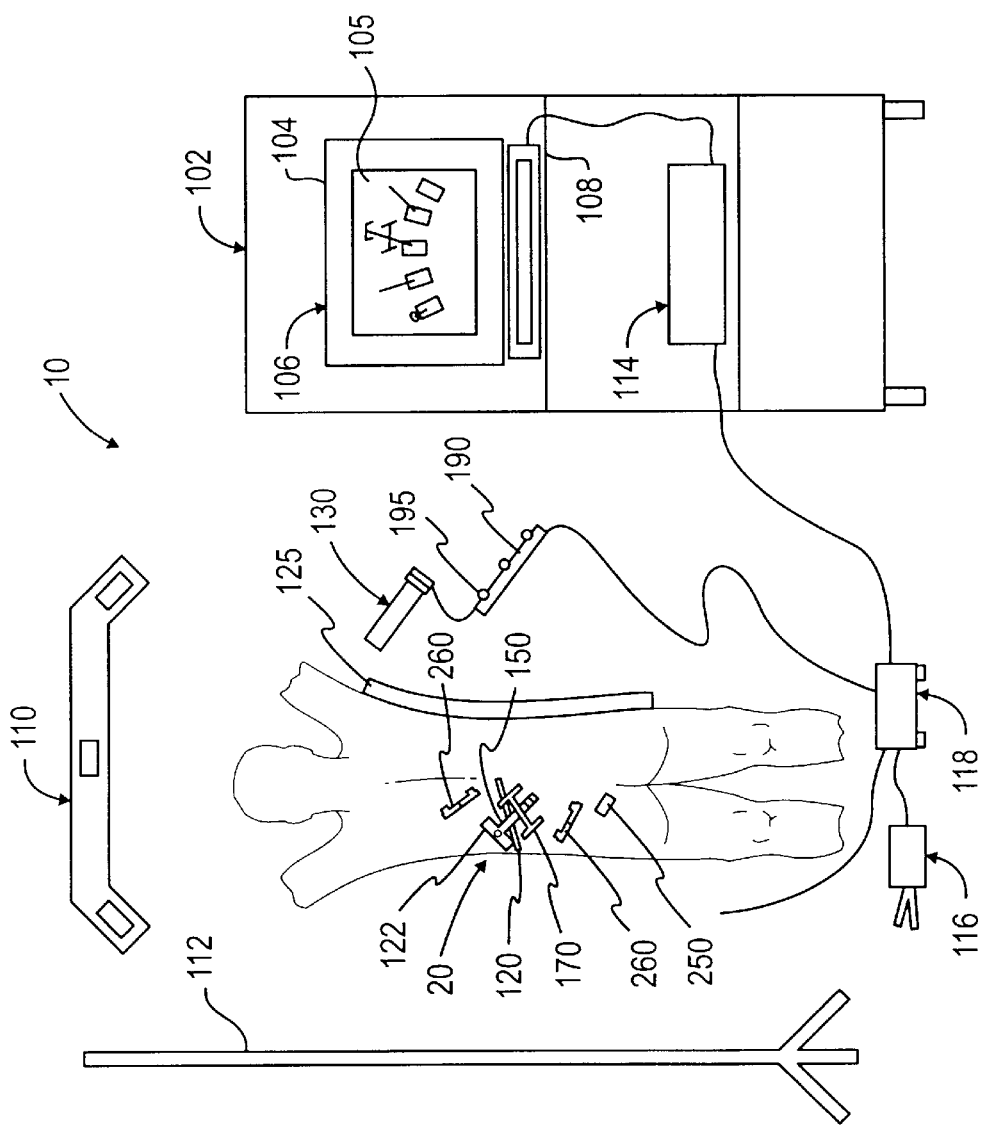
FIG. 1 is a schematic diagram of one preferred embodiment of a system, including a guide, a reference arc, a post, and wires placed in the spine for use with a surgical navigation system for spinal surgical procedures.

As generally described in PCT/US95/12894, the entire disclosure of which is incorporated herein by reference, a typical surgical navigation system is shown in FIG. 1. A computer assisted image guided surgery system, indicated generally at 10, generates an image for display on a monitor 106 representing the position of one or more body elements, such as spinal elements fixedly held in a stabilizing frame or device such as a spinal surgery frame 125 commonly used for spinal surgery. A reference arc 120 bearing tracking means such as for example LED emitters 122 is mounted to the spinous process by a clamp or other connecting device. The image is generated from an image data set, usually generated preoperatively by a CAT scanner for example, which image has reference points for at least one body element, such as a spinal element. The reference points of the particular body element have a fixed spatial relation to the particular body element. The system includes an apparatus such as a digitizer or other Position Sensing Unit (PSU), such as for example sensor array 110 on support 112 for identifying, during the procedure, the relative position of each of the reference points to be displayed by tracking the position of emitters 122 on arc 120. The system also includes a processor 114 such as a PC or other suitable workstation processor associated with controller 108 for modifying the image data set according to the identified relative position of each of the reference points during the procedure, as identified by array 110. The processor 114 can then, for example, generate a displaced image data set representing the position of the body elements during the procedure for display on monitor 106. In summary, the operation of a surgical navigating system is well known in the art and need not further be described here.

An embodiment of the present invention permits tracking without use of a clamp or other connecting device holding an emitter to a vertebral body by use of dynamic referencing (e.g. fluoroscopy referencing, magnetic resonance imaging intraoperatively, and ultrasonic registration). All of these options will show real time displacement and manipulation of the spine.

Figure 2:
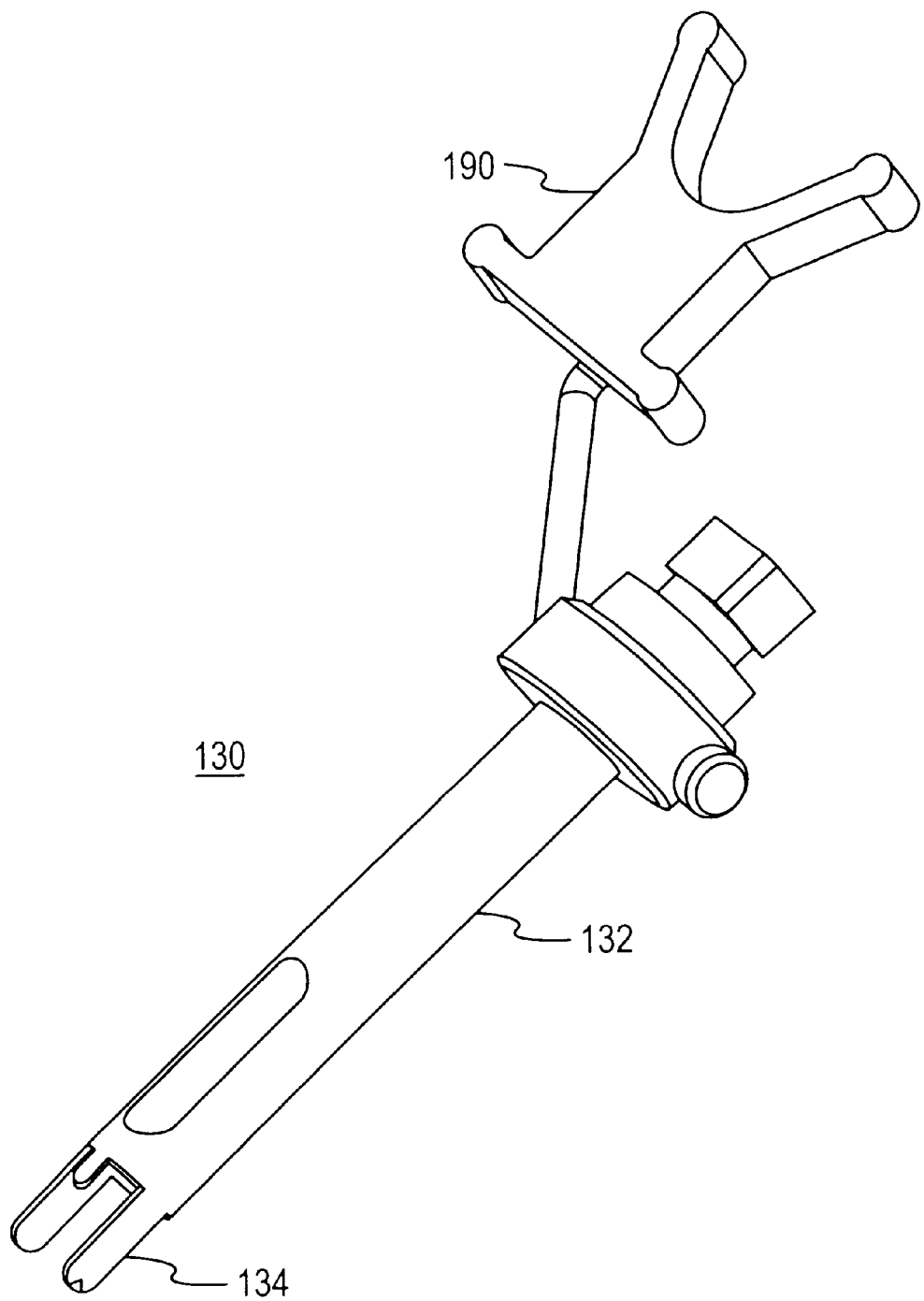
FIG. 2 is a perspective view of one preferred embodiment of a guide according to the present invention.
Figure 3:
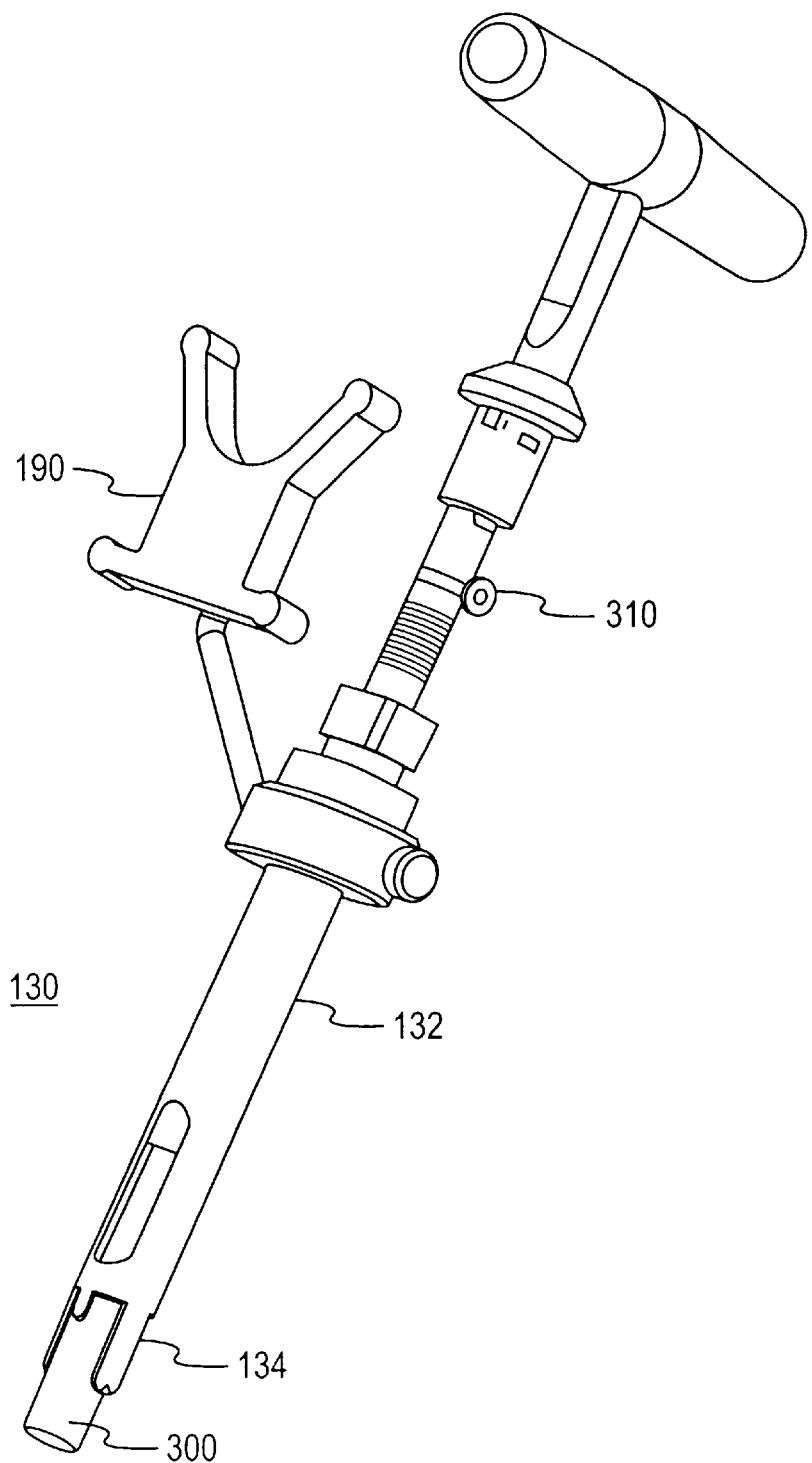
FIG. 3 is a perspective view of the guide of FIG. 2 with an instrument having an LED passing through the guide.
Figure 10:
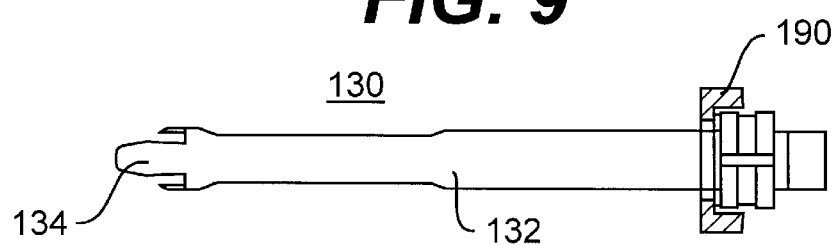
FIG. 10 is a side view of a guide having a disc penetrating extension and prong for engaging the adjacent vertebrae with attached emitter in cross-section.

In accordance with the preferred embodiment of the present invention, with further reference to FIGS. 2 and 3, the invention includes guide 130 for use in performing spinal surgery to prepare across a spinal disc and adjacent vertebrae an implantation space. Guide 130 is used in conjunction with computer controlled surgical navigation system 10 employing energy-detecting array 110 to track positions of guide 130 in three dimensional space relative to a known reference point. Guide 130 comprises body 132 for providing protected access to prepare the implantation space across the spinal disc and into the adjacent vertebrae. Body 132 has a passage adapted to receive a bone removal device, as shown in FIG. 3, for forming the implantation space through body 132. At least one emitter array 190 is attached to body 132 for use in identifying the location of guide 130 relative to the adjacent vertebrae. FIG. 10 shows an alternative guide 130 with disc penetrating extensions 134 and attached emitter array 190.

Figure 6A:
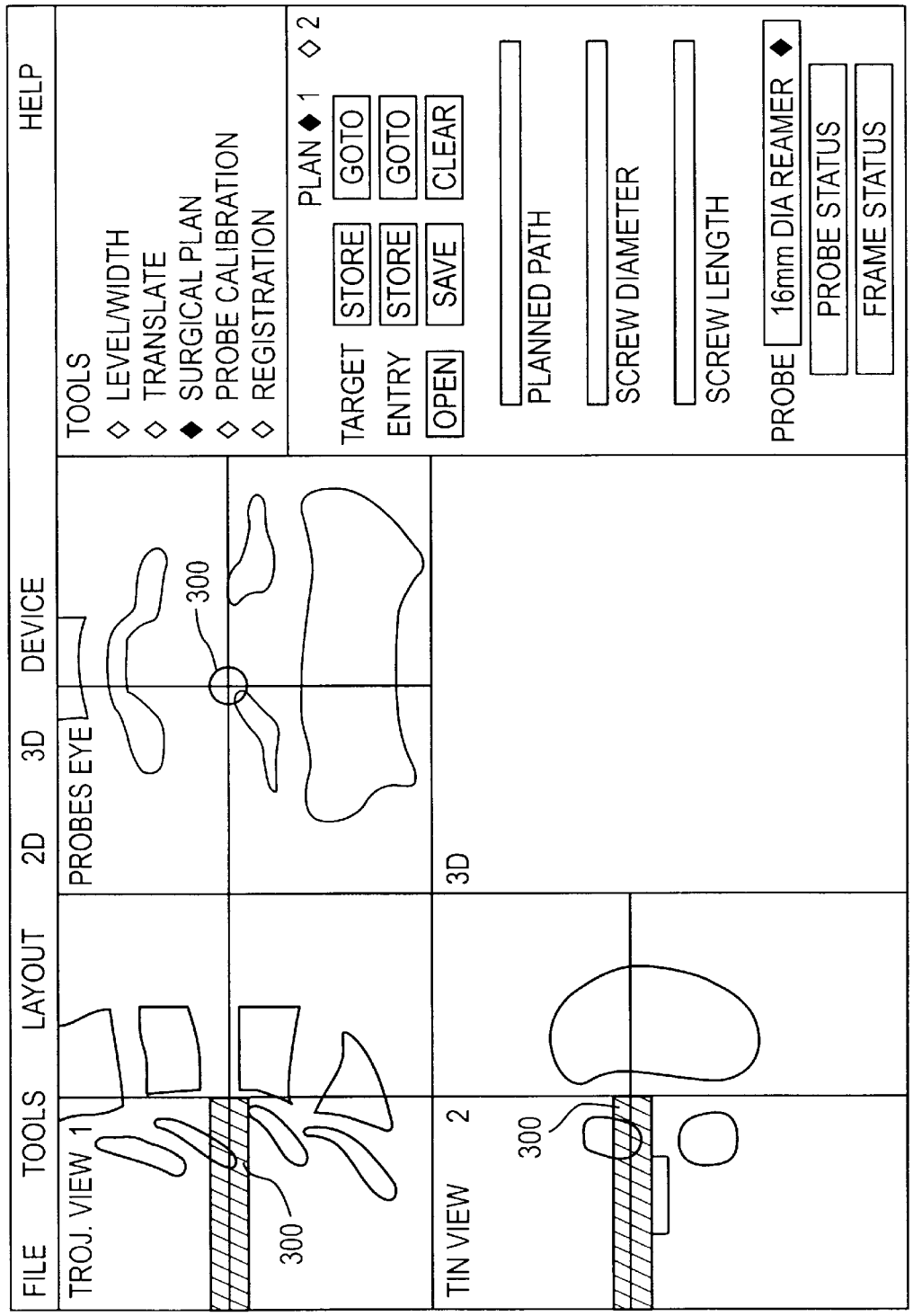
FIG. 6A depicts an image on a display screen produced in association with the guide, reamer passing through the guide, and surgical navigation system in accordance with a preferred embodiment of the present invention.
Figure 6B:
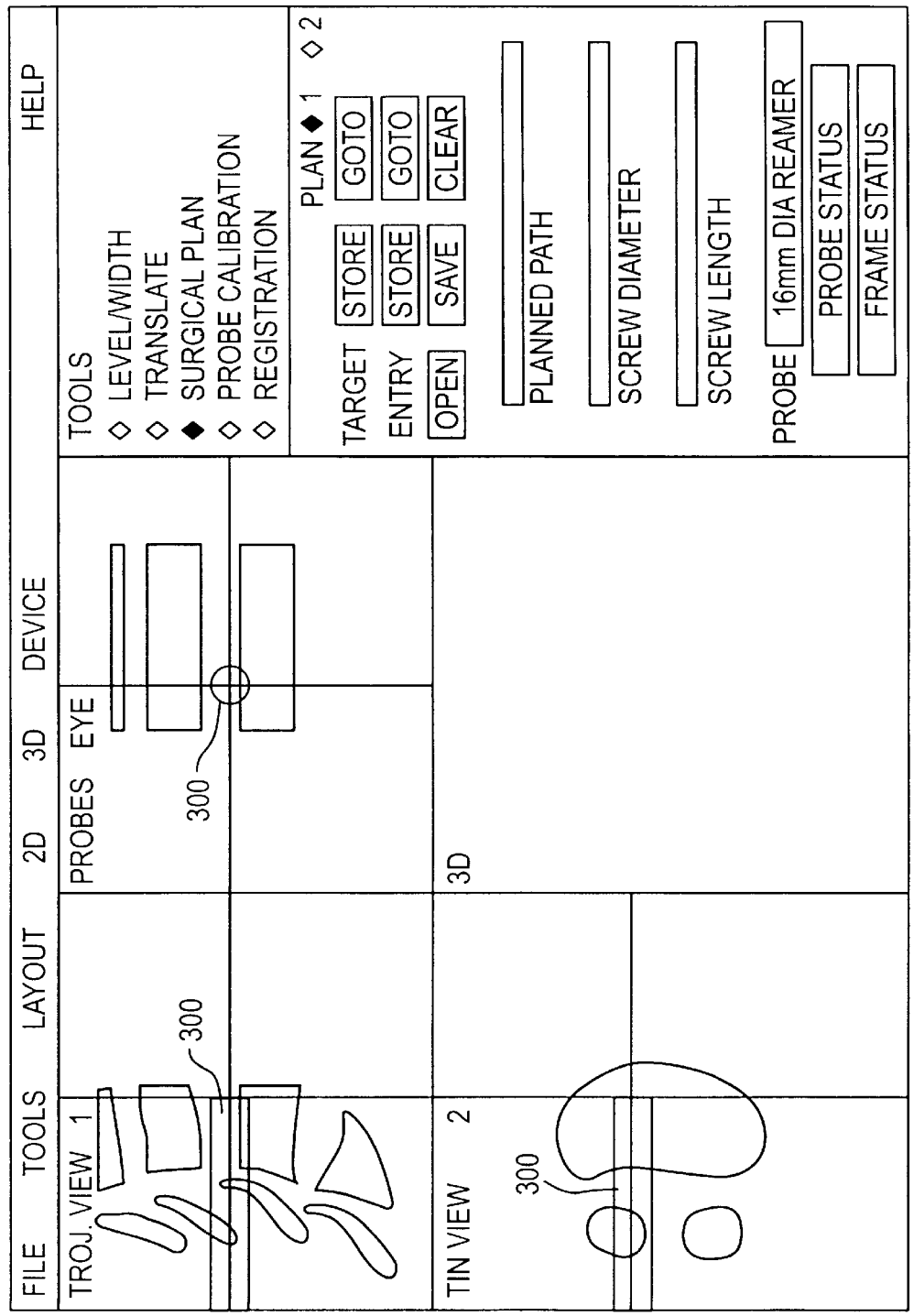
FIG. 6B depicts the embodiment of FIG. 6A with the reamer inserted deeper into the spine intervertebral disc space.

A preferred bone removal device includes a reamer 300 having a LED 310 as shown in FIGS. 3, 6A, and 6B. A visual display of the reamer 300 may be generated showing the depth of insertion of the reamer 300 into the spine relative to the known coordinates of the guide 130 and the body into which reamer 300 penetrates.

Figure 9:
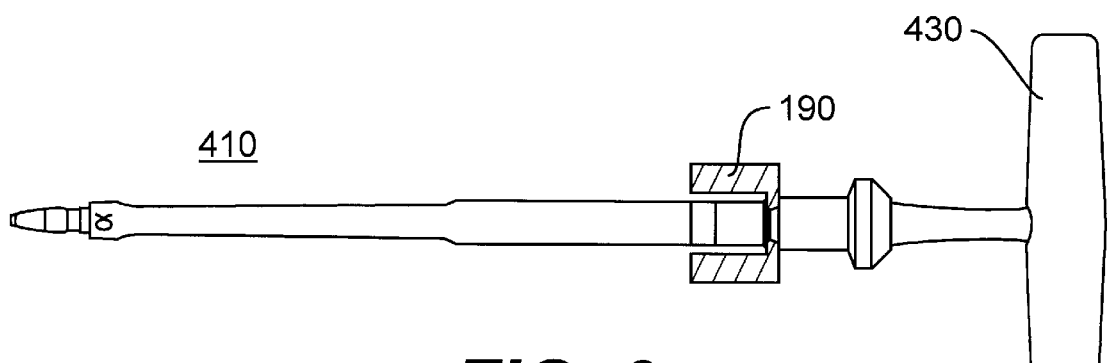
FIG. 9 is a side view of a distractor and T-handle assembly with attached emitter in cross-section.
Figure 11A:
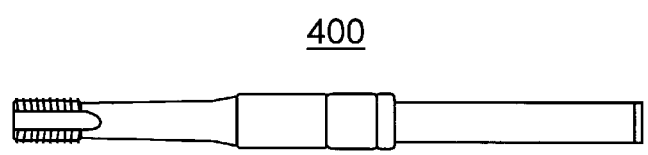
FIG. 11A is a side view of a tap.
Figure 11B:
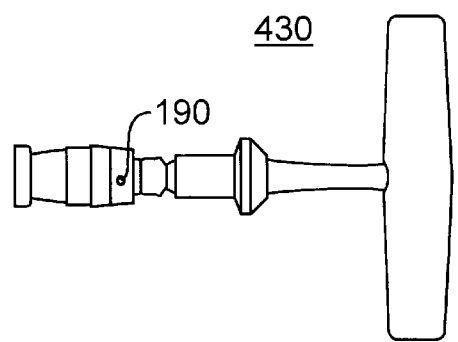
FIG. 11B is a side view of a T-handle with emitter.
Figure 12:
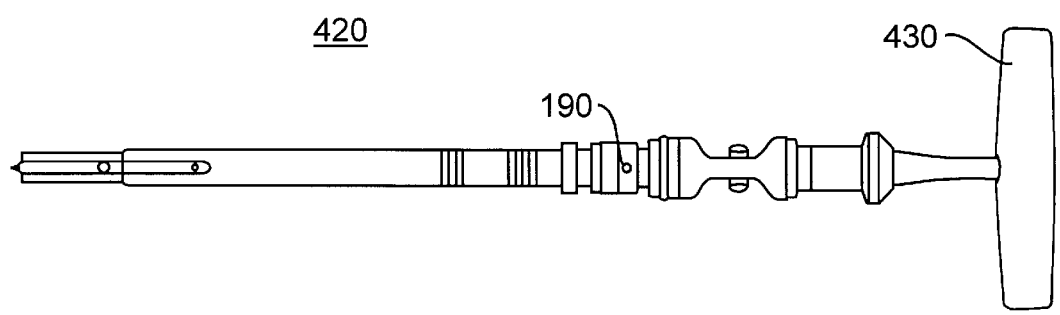
FIG. 12 is a side view of an inserter with attached T-handle and emitter.

Other devices for use in performing spinal surgery across the disc space are shown FIGS. 9, 11A, 11B, and 12. FIG. 9 depicts a distractor 410 with attached T-handle 430 and emitter 190. FIG. 11A shows a tap 400 which is preferably adapted for attachment to T-handle 430 shown in FIG. 11B. T-handle 430 includes an emitter 190 attached thereto for use in identifying the location of tap 400 relative to the adjacent vertebrae into which it is inserted. FIG. 12 shows an inserter 420 with attached T-handle 430 and emitter array 190. Emitter 190 on distractor 410, tap 400, and inserter 420, respectively is used to identify the location of each tool in three dimensional space relative to a known reference point so that each may be individually shown on the visual display associated with computer controlled surgical navigation system 10.

Guide 130 may additionally include a disc penetrating extension extending from body 132 for insertion into the disc space between the adjacent vertebrae and for bearing against endplates of the adjacent vertebrae. A preferred body 132 includes a hollow tube having an end including extensions 134 for penetrating the spine. A preferred emitter array 190 on the guide are light emitting diodes ("LEDs"), but can be any other energy radiating device or tracking means known in the art capable of being tracked by a corresponding detector array. A preferred emitter array includes three LEDs for use in determining location and rotation of a tool in space in all directions. For purposes of illustration, not limitation, the tracking means may generate signals actively such as with acoustic, magnetic, electromagnetic, radiologic, and micropulsed radar systems, or passively such as with reflective surfaces.

Additionally, the invention includes a system for use in performing spinal surgery to prepare across a spinal disc and adjacent vertebrae an implantation space. The system comprises the above described guide 130 and computer controlled surgical navigation system 10 employing an energy detecting array 110 to track positions of guide 130 in three dimensional space relative to a known reference point in a body similarly tracked by sensor array 110.

Guide 130 and computer controlled surgical navigation system 10 enable the spine surgeon to ensure the proper implantation of an implant or dowel by forming a properly oriented implantation space through guide 130 and into the spine as well as observe the depth of invention of instruments passing through guide 130. This outcome is ensured by properly orienting guide 130 prior to forming the implantation space. FIG. 4A shows a cross-sectional view of a spinal segment 200 having an implant or dowel 202 in a predetermined endplate 204 engagement. Typically, the preferred predetermined endplate 204 engagement occurs when approximately equal amounts of bone are removed from each of the adjacent endplates 204 of the adjacent vertebrae and the implant or dowel 202 is axially aligned from anterior A to posterior P or vise versa.

A cross-sectional view of a spinal segment having an implant or dowel 202 in a generally less desirable position is shown in FIG. 4B. The implant or dowel 202 depicted in FIG. 4B is shown implanted in an implantation space having an angled sagittal trajectory. In contrast, a generally preferred predetermined sagittal alignment of the implant or dowel 202 to the vertebrae is shown in FIG. 5B.

FIG. 5A shows a cross-sectional view of an implant or dowel 202 projected over an axial section of a vertebra and showing a predetermined axial alignment of the implant or dowel 202 to the vertebra from the posterior to the anterior. FIG. 5C is a cross-sectional view of an implant or dowel 202 positioned between adjacent vertebrae and showing a predetermined coronal alignment of the implant or dowel 202 to the vertebra. The proper placement of guide 130 prior to forming the implantation space enables the implant 202 to be placed in a predetermined axial, sagittal, and coronal orientation as depicted in FIGS. 5A, 5B, and 5C.

Once the surgeon registers the vertebral body with computer controlled surgical navigation system 10, the location of the above disclosed guide 130 can be viewed on the computer system relative to that body so that the spine surgeon can see in real time the location of the end of guide 130 in an axial, coronal, and sagittal view, as well as in a 3-D reconstruction. The surgeon will also be able to view the trajectory of guide 130 relative to this body in all three places. This technique clearly enhances the process for the surgeon to position guide 130 to form an implantation space and thereby optimize the positioning of the implant or dowel to be inserted.

In accordance with the display screens depicted in FIGS. 6A, 6B, 7, and 8, once a reference array is attached to the patient and registered, software within navigational system 10 provides the following information to the surgeon. The location of guide 130 is shown relative to the anatomy of the patient. The rotational position of guide 130 is also indicated to allow the surgeon to observe the orientation of guard extensions 134 relative to the adjacent vertebrae of the spine.

In particular, FIGS. 6A and 6B display reamer 300 inserted through guide 130 and show the depth of penetration of reamer 300. FIG. 6A shows reamer 300 just prior to removing material from the vertebrae endplates. FIG. 6B shows reamer 300 at a greater depth of insertion and after removal of material from the vertebrae endplates. The final position of reamer 300 remains on the display screen for reference by the surgeon. The diameter of the reamer 300 is preferably entered into the computer or selected from a programmed menu.

Figure 7:
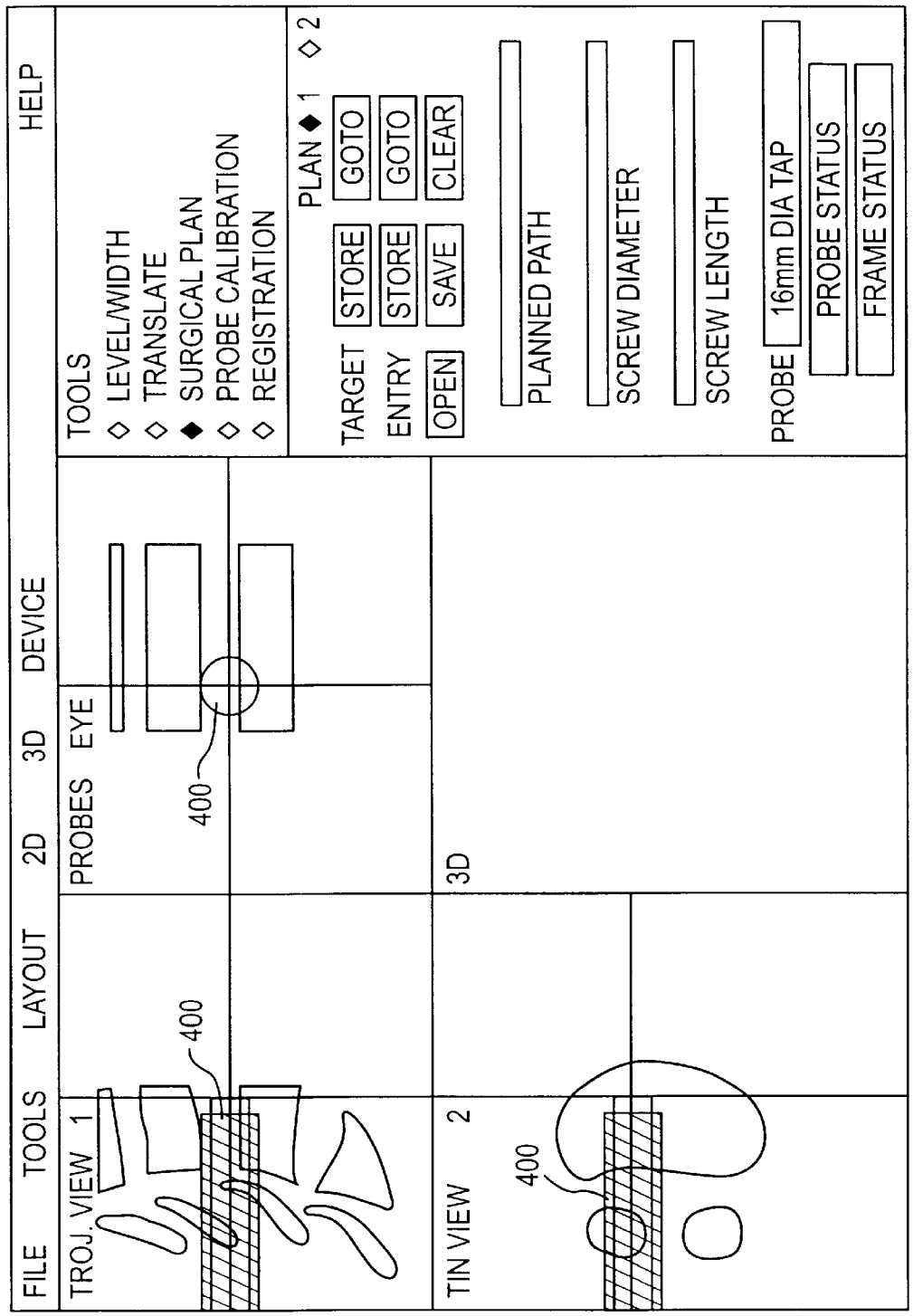
FIG. 7 depicts an image on a display screen produced in association with the guide, a tap passing through the guide, and surgical navigation system in accordance with another preferred embodiment of the present invention.

FIG. 7 depicts tap 400 being inserted through guide 130. The final position of tap 400 remains on the screen for reference by the surgeon. The diameter of tap 400 is entered into the computer or selected from a programmed menu.

Figure 8:
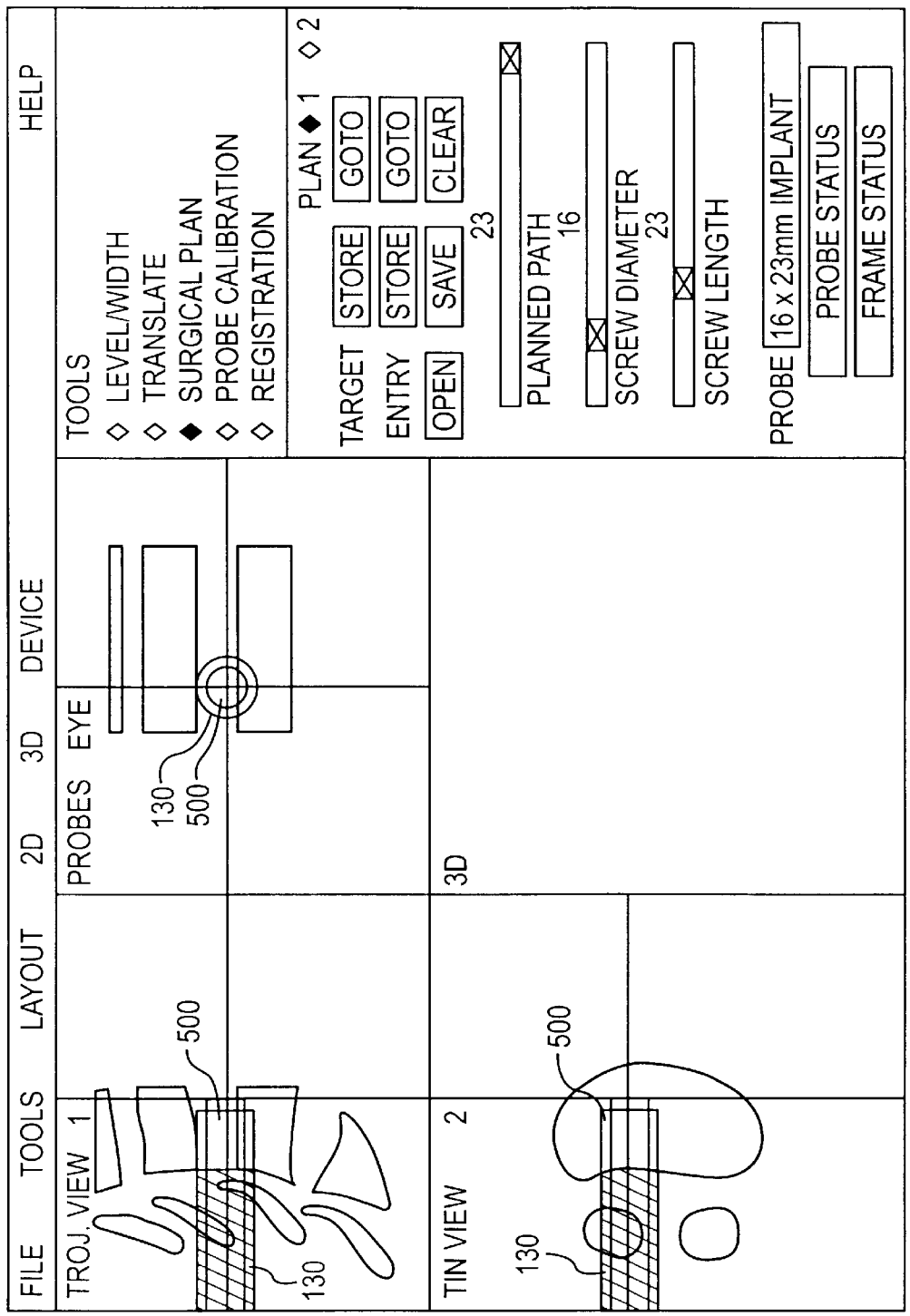
FIG. 8 depicts an image on a display screen produced in association with the guide, an implant passing through the guide, and surgical navigation system of yet another preferred embodiment of the present invention.

FIG. 8 shows a display representing the location and depth of implant 500 after insertion through guide 130. The final position of implant 500 remains on the screen for reference by the surgeon. Both the tip and tail of implant 500 is visible on the screen. The diameter and length of implant 500 is preferably entered into the computer or selected from a programmed menu.

By entering the dimensions of implant 500 into the computer or by selecting an implant size from a programmed menu and by having the geometric configuration of inserter 420 in the computer, the display can show the implant in relation to the adjacent vertebrae by knowing the position of the inserter and thereby knowing the position of a rigidly attached implant 500. In this manner, one can keep track of implant 500 or any other device of known dimension attached to a tool of known dimension having an emitter array attached thereto. By providing an emitter array on a tool of know dimension and tracking its position, the position of another device of known dimension rigidly attached to the tool can also be determined with certainty. Thus, the implant or other device can be displayed on the navigation system monitor without need for a separate emitter on the attached device.

Having described the preferred embodiment of the guide used in the present system, the method of using this apparatus to practice the invention will now be described. The operation of a surgical navigating system is generally well known and is described in PCT/US95/12894. The first step is to identify the location of the spine using computer-aided image guided surgical navigation methods.

A reference array 120 is rigidly attached to the vertebrae of interest. The attachment means can be a clamp, screw, or any other means. The reference array can be attached to a spinous process, for example, in a posterior case or to the anterior body in an anterior case. The array can be mounted percutaneously from a minimally invasive technique. Once the reference array is attached, the body of interest must be registered to the image data in the computer controlled surgical navigation system. This can be accomplished in many different ways. In an open or endoscopic case, points on the bone can be physically touched with a tracked pointer. For a percutaneous technique, points on a fiducial array which was attached to the body before the scan can be touched, or points on Fluoroscopic or Ultrasonic images can be identified. The invention may be used with any registration technique. The invention may also be used with any surgical technique (i.e. posterior, anterior, laparoscopic, anterior endoscopic, etc.)

Once the reference 120 is placed on the patient and the anatomy is registered with the computer system, guide 130 can be tracked in space relative to the spine in the surgical navigation system without further surgical exposure of the spine. The position of guide 130 is determined by the user stepping on a foot pedal 116 to energize the emitter array 190. The emitters 195 generate infrared signals to be picked up by camera digitizer array 110 and triangulated to determine the position of guide 130. The relative position of the body part, such as the spinal process is determined in a similar manner, through the use of similar emitters 122 mounted on the reference frame 120 in mechanical communication with the spinal segment. As is well known in this art and described in PCT/US95/12894, based upon the relative position of the spinal segment and guide 130 (such as by touching a known reference point) the computer would illustrate a preoperative scan—such as the proper CAT scan slice—on the screen of monitor 106 which would indicate the position of guide 130 and the spinal segment. It is also understood that passive as well as active tracking techniques can be used throughout.

After the spinal elements are registered in the spine, a guide can be properly oriented so that disc and bone may be removed through the guide to form a properly oriented implantation space into which an artificial implant or bone dowel may be inserted.

In addition, the invention further comprises a method for performing spinal surgery with a guide used to provide protected access across a spinal disc and into adjacent vertebrae to prepare an implantation space. The method comprises the following steps: contacting one end of the guide having at least one electrically energizable energy emitter array attached thereto to the adjacent vertebra; employing a surgical navigation system with a computer controller and a digitizer array for communicating with the energy emitter of the guide; positioning the guide in three dimensional space relative to a known reference point; and forming the implantation space through the guide across the disc space and into a portion of each of the adjacent vertebrae.

In another aspect, the method includes, the step of generating a display of the position of the guide. The generating step preferably displays the location of the guide relative to the adjacent vertebrae to provide a view of the axial orientation of the guide relative to each vertebra and/or relative to the adjacent vertebrae. The generating step may also display the location of the guide relative to the adjacent vertebrae to provide a cross-sectional view of the guide relative to one of an anterior or posterior view of the adjacent vertebrae. The generating step may also display the location of the guide relative to the adjacent vertebrae to provide a cross-sectional view of the guide in the sagittal and coronal planes or in planes relative to the current trajectory of the guide.

The method may also include the step of emitting a signal from an emitter attached to the guide which is received by an apparatus representatively indicating that signal on a visual display. A preferred method of the present invention also includes the step of implanting one of an artificial implant and a bone dowel into the implantation space.

It will be apparent to those skilled in the art that various modifications and variations can be made in the present invention and in construction of this guide in association with a surgical navigation system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. A system for use in performing spinal surgery to prepare across a spinal disc and adjacent vertebrae an implantation space, said system comprising:

a guide for providing access to prepare the implantation space across the spinal disc and into the adjacent vertebrae, said guide having a passage adapted to receive a tool through said guide for forming the implantation space, said guide having at least one emitter array attached thereto for use in identifying the location of said guide relative to the adjacent vertebrae;

a computer controlled surgical navigation system employing an energy detecting array to track positions of said guide in three dimensional space relative to a known reference point;

an inserter sized for passage through said guide, said inserter having at least one emitter array attached thereto for use in identifying the location of said inserter relative to the adjacent vertebrae, said inserter adapted to hold one of an artificial implant and a bone dowel for insertion into the implantation space; and wherein said computer controlled surgical navigation system tracks the position of said inserter in a three dimensional space relative to a known reference point, and said computer controlled surgical navigation system generates a display of the position of said inserter; and wherein said computer controlled surgical navigation system displays one of an artificial implant and a bone dowel on the end of said inserter based on the geometrical configuration of said inserter and of the one of the artificial implant and a bone dowel attached to said inserter being entered into said computer controlled system.

2. The system of claim 1, wherein said emitter array includes at least one LED.

3. The system of claim 1, wherein said emitter array is an electrically energizable energy emitter array.

4. The system of claim 1, wherein said emitter array emits reflective signals.

5. The system of claim 1, wherein said emitter extends to the side of said guide to provide a line of sight from said emitter to the energy-detecting array of the navigation system.

6. The system of claim 1, wherein said guide comprises a hollow tube.

7. The system of claim 6, wherein said hollow tube has a rectangular cross-section.

8. The system of claim 6, wherein said guide further comprises spikes for engaging the adjacent vertebrae to inhibit displacement of the adjacent vertebrae during preparation of the implantation space.

9. The system of claim 1, wherein said guide has an end including extensions for penetrating the spine.

10. The system of claim 1, wherein said guide further comprises a disc penetrating extension extending from said guide for insertion into the disc space between the adjacent vertebrae and for bearing against endplates of the adjacent vertebrae.

11. The system of claim 1, further comprising said tool, wherein said tool has an energy emitter for use in identifying the depth of penetration of said tool through said guide.

12. A method for performing spinal surgery with a guide used to provide protected access across a spinal disc and into adjacent vertebrae to prepare an implantation space, said method comprising:

contacting one end of said guide having at least one emitter array attached thereto to the adjacent vertebrae;

employing a surgical navigation system with a computer controller and a digitizer array for communicating with said emitter array of said guide;

positioning said guide in three dimensional space relative to a known reference point;

forming the implantation space through said guide across the disc space and into a portion of each of the adjacent vertebrae;

implanting one of an artificial implant and a bone dowel into the implantation space;

providing an inserter sized for passage through said guide, said inserter having at least one emitter array attached thereto for use in identifying the location of said inserter relative to the adjacent vertebrae, said inserter adapted to hold one of an artificial implant and a bone dowel for insertion into the implantation space; and generating a display of the position of said inserter relative to the adjacent vertebrae to provide a view of the axial orientation of said inserter relative to the adjacent vertebrae;

wherein the generating displays one of an artificial implant and a bone dowel on the end of said inserter.

13. The method of claim 12, wherein the contacting includes contacting one end of a tubular member having at least one emitter array attached thereto to the adjacent vertebrae.

14. The method of claim 12, wherein the positioning includes the step of positioning said guide in three dimensional space relative to a known reference point in the adjacent vertebrae.

15. The method of claim 12, further comprising positioning into the disc space between the adjacent vertebrae said guide having an extension for insertion into the disc space and for bearing against end plates of the adjacent vertebrae.

16. The method of claim 12, further comprising generating a display of the position of said guide.

17. The method of claim 16, wherein the generating displays the location of said guide relative to the adjacent vertebrae to provide a view of the axial orientation of said guide relative to each vertebra.

18. The method of claim 16, wherein the generating displays the location of said guide relative to the adjacent vertebrae to provide a view of the axial orientation of said guide relative the adjacent vertebrae.

19. The method of claim 16, wherein the generating displays the location of said guide relative to the adjacent vertebrae to provide a cross-sectional view of said guide relative to one of an anterior or posterior view of the adjacent vertebrae.

20. The method of claim 12, further comprising emitting a signal from said emitter attached to said guide which is received by an apparatus representatively indicating that signal on a visual display.

21. The method of claim 12, further comprising reflecting a signal from said emitter attached to said guide which is received by an apparatus representatively indicating that signal on a visual display.

22. The method of claim 12, wherein forming the implantation space includes passing a tool having an energy emitter through said guide.

* * * * *